(12) United States Patent
Wollschläger

(10) Patent No.: US 6,986,749 B2
(45) Date of Patent: Jan. 17, 2006

(54) DEVICE FOR INSERTING A GUIDE WIRE AND/OR FOR HANDLING A CATHETER SHAFT

(76) Inventor: Helmut Wollschläger, Gabrielistraße 9, D-90480 Nürnberg (DE)

( * ) Notice: Subject to any disclaimer, the term of this patent is extended or adjusted under 35 U.S.C. 154(b) by 386 days.

(21) Appl. No.: 10/117,504

(22) Filed: Apr. 5, 2002

(65) Prior Publication Data

US 2002/0169396 A1 Nov. 14, 2002

Related U.S. Application Data

(63) Continuation of application No. PCT/DE00/02944, filed on Aug. 25, 2000.

(30) Foreign Application Priority Data

Oct. 7, 1999 (DE) .......................... 199 48 409

(51) Int. Cl.
*A61B 5/04* (2006.01)

(52) U.S. Cl. ........................ 600/585; 604/159
(58) Field of Classification Search ................ 604/249, 604/246, 528; 600/585
See application file for complete search history.

(56) References Cited

U.S. PATENT DOCUMENTS

| | | | |
|---|---|---|---|
| 4,716,757 A | | 1/1988 | McGregor et al. |
| 5,159,861 A | | 11/1992 | Anderson |
| 5,318,541 A | | 6/1994 | Viera et al. |
| 5,338,313 A | * | 8/1994 | Mollenauer et al. ........ 604/249 |
| 5,427,118 A | | 6/1995 | Nita et al. |
| 5,443,078 A | | 8/1995 | Uflacker |
| 5,921,968 A | * | 7/1999 | Lampropoulos et al. .... 604/246 |

FOREIGN PATENT DOCUMENTS

| | | |
|---|---|---|
| DE | 195 26 075 C1 | 12/1996 |
| JP | 10-151204 | 6/1998 |

* cited by examiner

*Primary Examiner*—Max F. Hindenburg

(57) ABSTRACT

The invention relates to a device for handling at least one guide wire (51) in order to guide an invasive medical instrument or in order to handle a catheter shaft using invasive medical techniques. A fixing arm (13) which can be fixed to an introduction valve (1) and a clamping device (16) attached to the fixing arm (13) are provided, wherewith the relevant guide wire or the catheter shaft can be secured against movements in the longitudinal direction. This enables the introduction valves (1) to be operated with one hand, while the other hand can be used for the manipulation of the other invasive medical instruments as opposed to having to fix elements such as a guide wire or catheter shaft which cannot be moved in a longitudinal direction.

24 Claims, 16 Drawing Sheets

DEVICE FOR INSERTING A GUIDE WIRE AND/OR FOR HANDLING A CATHETER SHAFT

CROSSREFERENCES TO RELATED APPLICATIONS

This application is a continuation of copending international patent application PCT/DE00/02944 filed on Aug. 25, 2000 and designating the U.S., which claims priority of German patent application DE 199 48 409 filed on Oct. 7, 1999.

BACKGROUND OF THE INVENTION

The invention relates to a device for handling at least one guide wire in order to guide an invasive medical instrument or for handling a catheter shaft in invasive medical techniques.

Devices for handling guide wires are, for example, disclosed in U.S. Pat. No. 5,159,861, U.S. Pat. No. 5,427,118, U.S. Pat. No. 5,318,541, U.S. Pat. No. 4,716,757 or U.S. Pat. No. 5,443,078.

In current practice in invasive medical techniques, for example in invasive cardiology or invasive radiology, an introduction valve is used which, for example in invasive cardiology, is attached to a guide catheter which is inserted from the groin area, for example, as far as the pericardial region of the aorta. Depending on patient-specific requirements, at least one guide wire is inserted in a manner known per se through the introduction valve and into the guide catheter, which guide wire reaches with its distal end as far as the ends of the vessels to be treated, and at least one invasive medical instrument is also inserted, for example, in the case of invasive cardiology, a dilation catheter for treatment of stenoses. After the guide wire has been fitted in place, it must no longer be able to move in the longitudinal direction at any time during the intervention in order, on the one hand, to avoid injuries in the end area of the vessels and, on the other hand, to guarantee unimpeded access to the treatment area throughout the intervention. The operating physician achieves this by gripping the guide wire between two fingers and thus preventing its longitudinal displacement during manipulation of an invasive medical instrument, for example an inserted dilation catheter, with the introduction valve opened.

However, in invasive surgery, this procedure has been found to be relatively awkward and has proven problematic for the patient, especially in view of the fact that longitudinal displacement of the guide wire are sometimes unavoidable even with the greatest care being taken.

SUMMARY OF THE INVENTION

The object of the invention is to make available a device for handling at least one guide wire in order to guide an invasive medical instrument or for handling a catheter shaft in invasive medical techniques, said device making it easier for the physician performing the invasive procedure to manipulate the invasive instruments during an operation.

According to the invention, this object is achieved with a device for handling at least one guide wire in order to guide an invasive medical instrument or a catheter shaft in invasive medical techniques, with a fixing arm which can be secured on an introduction valve, and with a clamping device which is arranged on the fixing arm and with which the particular guide wire or catheter shaft can be secured against longitudinal displacement.

Providing a fixing arm, with a clamping device arranged on said fixing arm, for securing a guide wire or catheter shaft against longitudinal displacement means that, after inserting a guide wire or after fitting an invasive medical instrument to be at least temporarily fixed, for example a catheter, the physician who is performing the invasive procedure is no longer obliged, during the operation, to fix the guide wire or a catheter shaft assigned to the invasive medical instrument, and can instead devote his complete attention to other work, such as actuating the introduction valve with one hand and manipulating an invasive medical instrument with the other hand. In this way, the risks to a patient in invasive medical techniques are greatly reduced.

In a preferred embodiment of the device according to the invention, the fixing arm can be secured on the introduction valve in a releasable manner via a groove-and-tongue connection. In a further preferred embodiment of the device according to the invention, the fixing arm can be secured on the introduction valve in a releasable manner via a plug connection. In one configuration of the latter embodiment, an adapter piece is provided with which the fixing arm can be secured in a releasable manner on the introduction valve. In this way, a relatively simple arrangement of the fixing arm on the introduction valve is obtained.

In a further preferred embodiment, the fixing arm is connected rigidly to the introduction valve. In this embodiment, it is guaranteed that the fixing arm cannot under any circumstances detach itself from the introduction valve during the intervention.

To ensure easy fixing, it is expediently provided that the fixing arm protrudes beyond an introduction end of the introduction valve. In this way, the elements to be fixed are held in a relatively rectilinear manner and strong bending is avoided.

In the last-mentioned configuration, it is further expedient for the fixing arm to have a securing portion and a holding portion which is angled off in relation to the securing portion. In this way, the area adjacent to the introduction end of the introduction valve remains relatively easily accessible.

In order to be able to use a clamping device with a plurality of clamping units, it is expedient for the fixing arm to have a securing portion and a holding portion designed as a holding plate.

With a view to obtaining a configuration which is as compact as possible, it is expedient for the clamping device to have a clamping unit for fixing a guide wire.

If a plurality of elements are to be fixed, it is expedient for the clamping device to have at least two clamping units which are arranged laterally spaced apart from one another and are used for fixing two guide wires or one guide wire and a catheter shaft. In this connection, it is particularly advantageous if the clamping device has three or four clamping units which are arranged laterally spaced apart from one another and are used for fixing guide wires and/or catheter shafts.

In one embodiment, the clamping device has, as clamping unit, at least one elongate clamping rail which has a holder part with a base plate and two side cheeks and has a clamping body inserted into the holder part and designed with a longitudinally extending clamping slit. In this way, sufficiently high frictional forces are exerted in particular on a generally relatively smooth guide wire.

In one configuration of the last-mentioned embodiment, it is expedient, with a view to obtaining a mechanically simple construction, if the base plate and the side cheeks are connected rigidly to one another and at right angles to one another.

According to a further configuration, in particular where the elements to be fixed by clamping rails according to the last-mentioned embodiment have relatively thick cross sections, it is expedient for each of the side cheeks to be arranged pivotably on the base plate via a respective hinge, and for a locking device to be provided for fixing them with the clamping slit closed.

In an expedient embodiment of the locking device, said locking device has two snap-fit lugs which engage one behind the other in the closed position of the side cheeks.

In a further preferred embodiment of the locking device, said locking device has a tilting bracket which at one end is articulated on one side cheek and, in the closed position, engages over the other side cheek.

To increase the frictional forces in a clamping slit, it is expedient for the clamping slit to be undulating.

In embodiments for increasing the frictional forces in a clamping slit, it is further provided that the clamping body has slits which are oriented transversely or obliquely with respect to the clamping slit.

In a further configuration of a clamping device, said clamping device has at least one clamping sleeve arrangement with a clamping sleeve and a screw sleeve which are designed with grooves that can be aligned relative to one another and are intended to receive a guide wire or a catheter shaft, the cross section of the clamping sleeve decreasing at least in stages in a direction of rotation.

In this configuration, the frictional forces exerted on the inserted elements can be advantageously adjusted.

In a further configuration of a clamping device, said clamping device has a counterplate and a rotatably mounted pivot body which, in a first pivot position, is at a distance from the counterplate, and, in a second pivot position, bears in part on the counterplate.

In another embodiment in this respect, the pivot body has a circular cross section and is mounted eccentrically.

In a further embodiment in this respect, the pivot body has an elliptical cross section. In the embodiment with a pivot body having an elliptical cross section, the pivot body is mounted centrally. In a further embodiment with a pivot body having an elliptical cross section, the pivot body is mounted in the area of a focal point.

The configuration and related embodiments with a pivot body are distinguished by particularly reliable fixing on account of the utilization of the lever action.

BRIEF DESCRIPTION OF THE DRAWINGS

Further expedient configurations of the invention are the subject of the dependent claims and of the following description of illustrative embodiments of the invention with reference to the figures in the drawing, where:

DETAILED DESCRIPTION OF PREFERRED EMBODIMENTS

Figure 1:
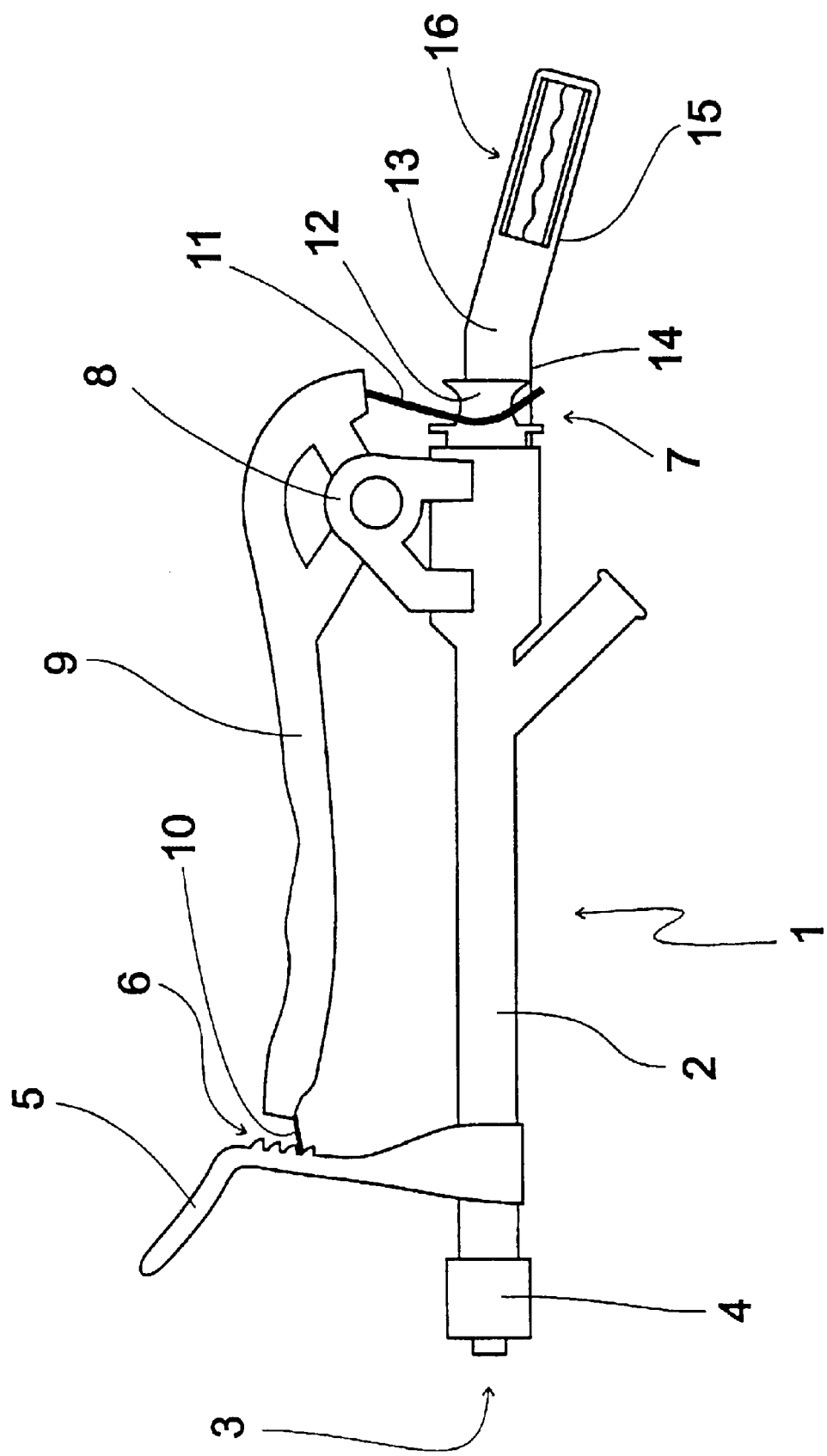
FIG. 1 shows a side view of an introduction valve with a fixing arm which is arranged thereon and on which a clamping rail is arranged.

FIG. 1 shows a side view of an introduction valve 1 which, because it is operated with one hand, is used particularly advantageously in conjunction with the invention and has an elongate valve body 2. At an attachment end 3, the valve body 2 is equipped with a screw sleeve 4 which can be screwed onto a guide catheter not shown in FIG. 1. Arranged on the valve body 2 in the area of the attachment end 3 there is a flexible locking arm 5 which has a number of catches 6. Moreover, in the area of an introduction end 7 remote from the attachment end 3, there is a bearing piece 8 which is secured on the valve body 2 and on which a handle 9 is rotatably mounted. Arranged at the end of the handle 9 remote from the bearing piece 8 there is a locking tongue 10 which engages with the catches 6 when the handle 9 is in approximately parallel alignment with the valve body 2.

The handle 9 is used to actuate a tongue 11 of metal or plastic which engages with a pressure piston 12 inserted into the valve body 2 at the introduction end 7. In the introduction position of the handle 9 shown in FIG. 1, an introduction opening is freed through which it is possible to introduce, for example, a guide wire for invasive instruments used in the area of invasive medical techniques, for example invasive catheters such as dilation catheters in invasive cardiology or corresponding instruments in invasive radiology or drills or reamers, and, after placement of the guide catheter, the relevant invasive instrument itself.

Finally, a side tube opens into the valve body 2 at an acute angle approximately in the area of the bearing piece 8, and a manometer can be attached to this side tube in a manner known per se in order to monitor the pressure conditions.

It will be understood that differently configured introduction valves, for example equipped with a rotary closure piece for closing the introduction end 7, can also be used in connection with the invention.

In the illustrative embodiment according to FIG. 1, a fixing arm 13 is arranged on the valve body 2 of the introduction valve 1, which fixing arm 13 has a securing portion 14 aligned with the longitudinal axis of the valve body 2 and connected to the valve body 2, and also a holding portion 15 which is angled off in relation to the securing portion 14. Arranged on the holding portion 15, as clamping device for a guide wire, there is an elongate clamping rail 16 as clamping unit, with which the guide wire or a catheter shaft of an invasive instrument can be secured against longitudinal displacements.

Figure 2:
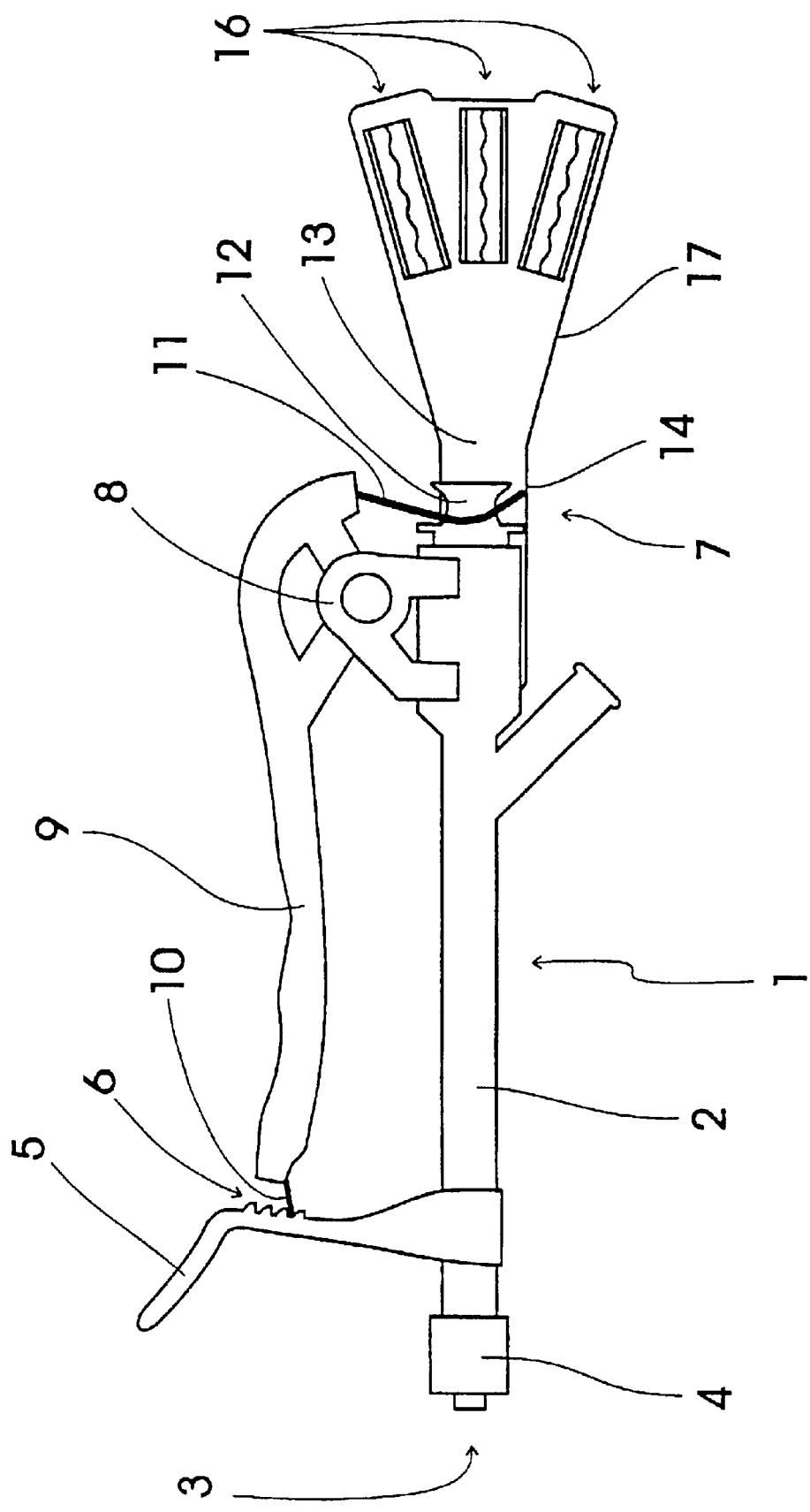
FIG. 2 shows a side view of an introduction valve with a fixing arm which is arranged thereon and on which three clamping rails are arranged.

FIG. 2 shows a side view of an introduction valve 1 according to FIG. 1 with a fixing arm 13 on which three clamping rails 16 are arranged on a holding plate 17 adjoining the securing portion 14. The three clamping rails 16 can be used, for example, to secure two guide wires and a guide portion of an invasive instrument, or a guide wire and guide portions of two invasive instruments, against longitudinal displacements.

Figure 3:
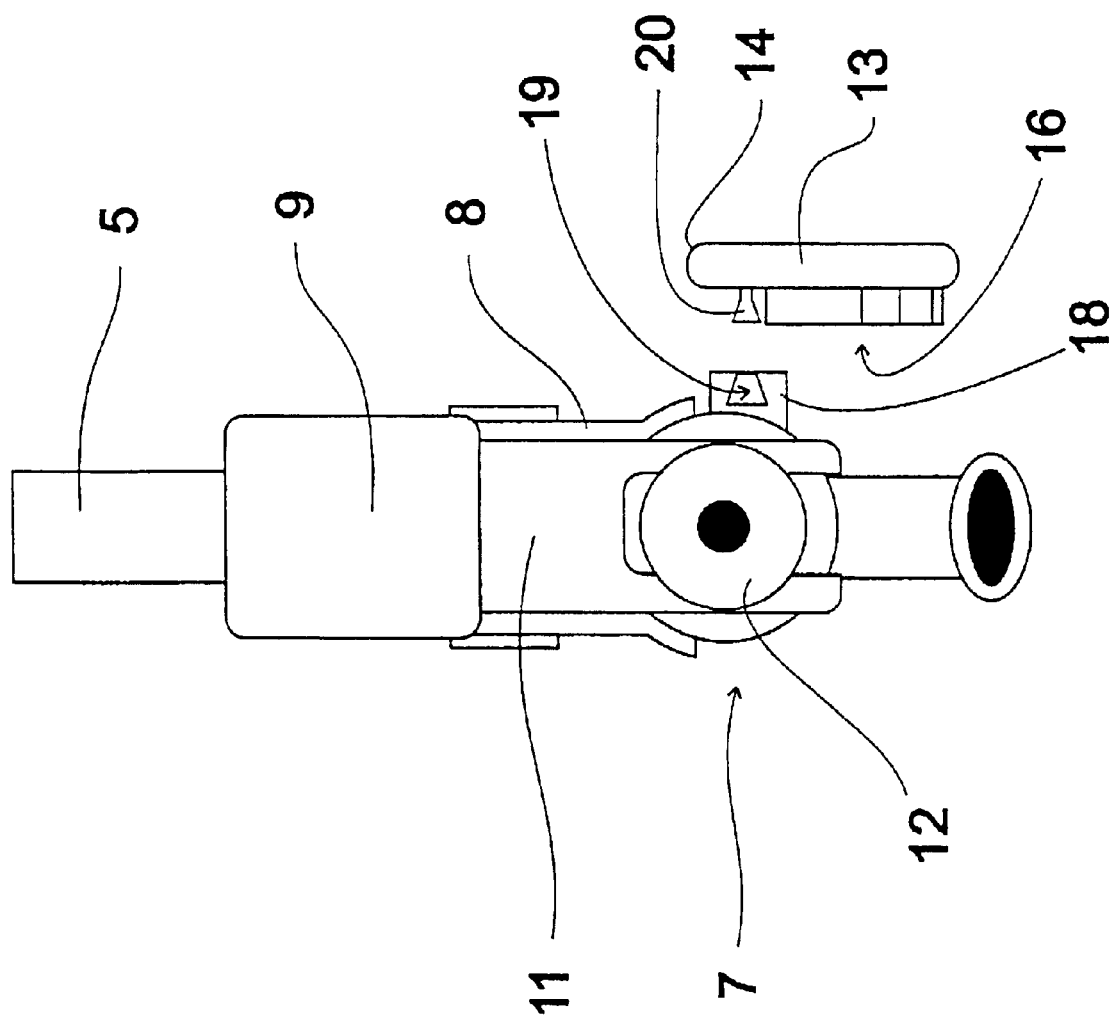
FIG. 3 shows a rear view of an introduction valve according to FIG. 1 and FIG. 2.

FIG. 3 shows a rear view of the introduction end 7 of an introduction valve 1 according to FIG. 1 and FIG. 2, and also the fixing arm 13 according to FIG. 1. It can be seen from FIG. 3 that a plug-in rail 18 is formed on the valve body 2 and has a groove 19 tapering towards its opening. On the securing portion 14 of the fixing arm 13 there is a web 20 which has a shape complementing the cross section of the groove 19. The introduction valve 1 and the fixing arm 13 can thus be connected releasably to one another in the manner of a groove-and-tongue connection.

Figure 4:
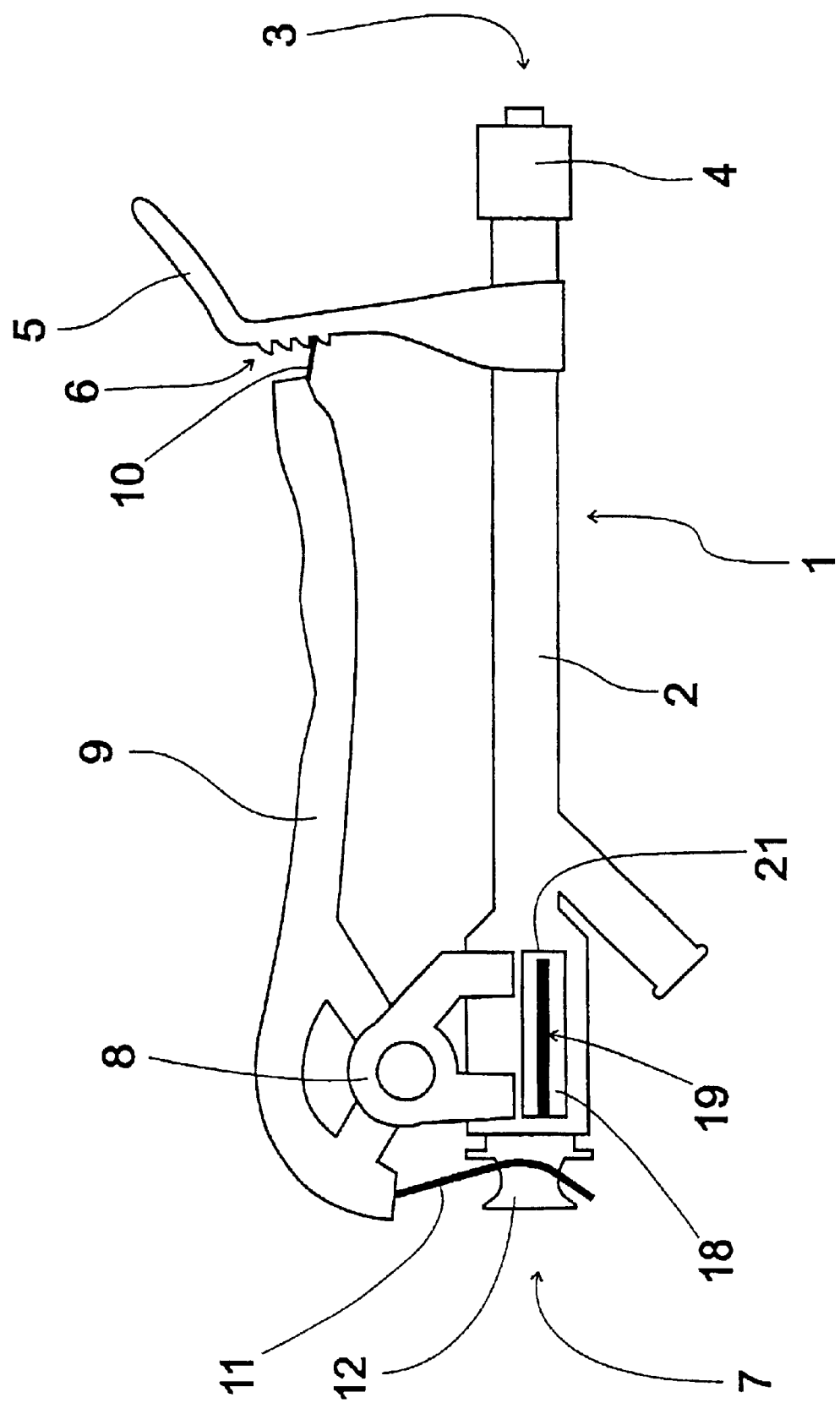
FIG. 4 shows a side view of an introduction valve according to FIG. 1 and FIG. 2, with the fixing arm removed.

FIG. 4 shows a side view of an introduction valve 1 according to FIG. 1 and FIG. 2, with the fixing arm 13 removed. It can be seen from FIG. 4 that the plug-in rail 18 has a length which leads to the fixing arm 13 being mounted in a manner free from play. At the end directed away from the introduction end 7, the groove 19 of the plug-in rail 18 is terminated by a closure wall 21 on which the web 20 of the support arm 13 strikes after substantially complete insertion into the groove 19, so that inadvertent pushing through is prevented.

Figure 5:
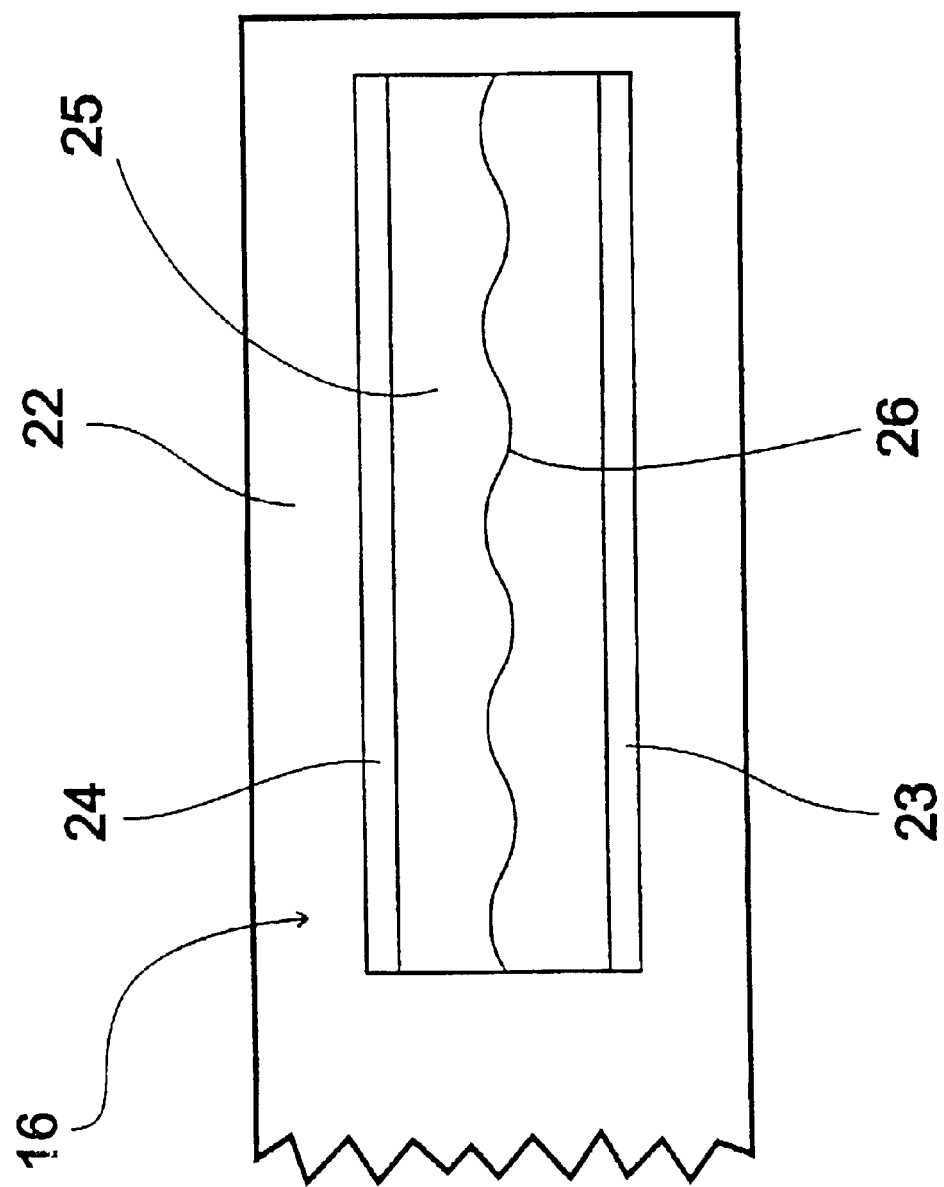
FIGS. 5 and 6 show a plan view and an end view, respectively, of a clamping rail with clamping body according to FIG. 1 and FIG. 2, respectively.
Figure 6:
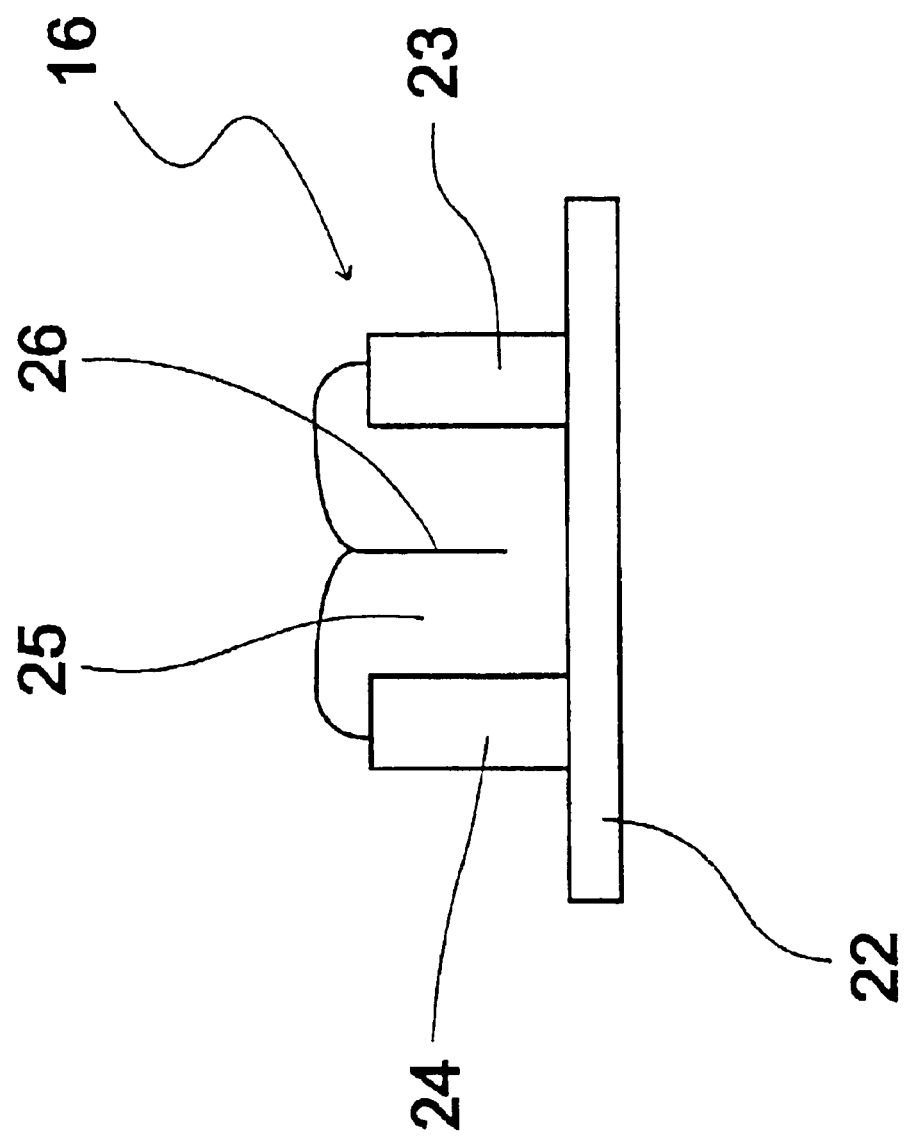

FIG. 5 and FIG. 6 show, in a plan view and end view, respectively, a clamping rail 16 according to FIG. 1 and FIG. 2. The clamping rail 16 has, as holder part, a base plate 22 which is formed through the holding portion 15 and the holding plate 17 of the fixing arm 13 and on which a first elongate side cheek 23 and a second elongate side cheek 24 are arranged at right angles thereto. Inserted between the side cheeks 23, 24 there is a clamping body 25 which is made of a relatively soft compressible material, for example silicone, with a high coefficient of static friction. A clamping slit 26 is incorporated in the clamping body 25, approximately centrally in the longitudinal direction, into which clamping slit 26 a guide wire, for example, can be inserted. The clamping slit 26 in the clamping body 25 is advantageously of undulating configuration, as is shown in FIG. 5, in order to increase the frictional forces exerted on an inserted, relatively smooth and stiff guide wire.

It can be seen from FIG. 6 that the clamping slit 26 advantageously ends at a distance from the base plate 22 in order to keep the clamping body 25 in a single piece for simpler handling.

It will be appreciated that, in modifications of the above, the clamping slit 26 can also be made continuous and the clamping body 25 can be made in two parts.

Figure 7:
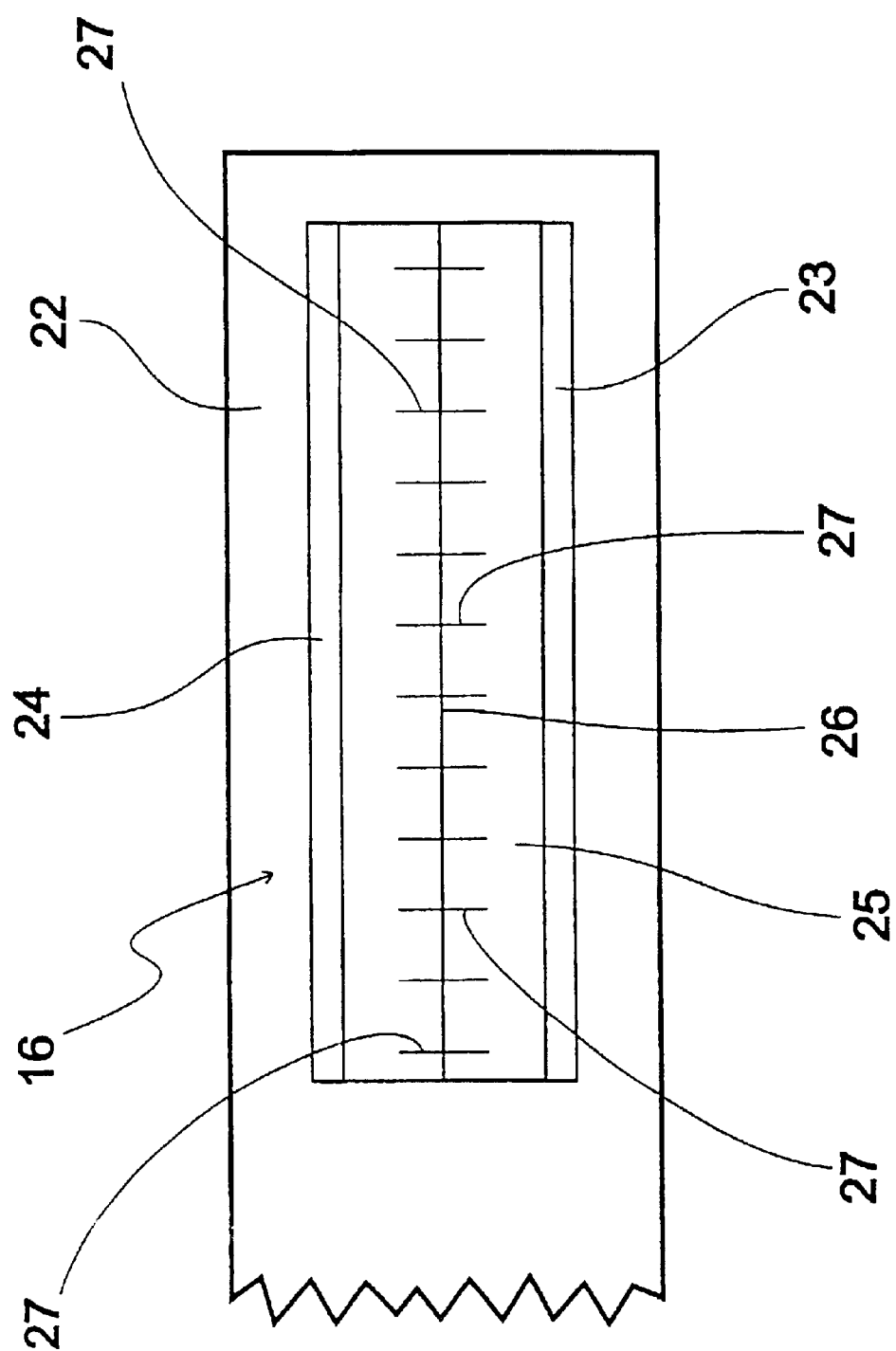
FIGS. 7 and 8 show, each in a plan view, further configurations of clamping bodies for clamping rails according to FIG. 1 and FIG. 2.
Figure 8:
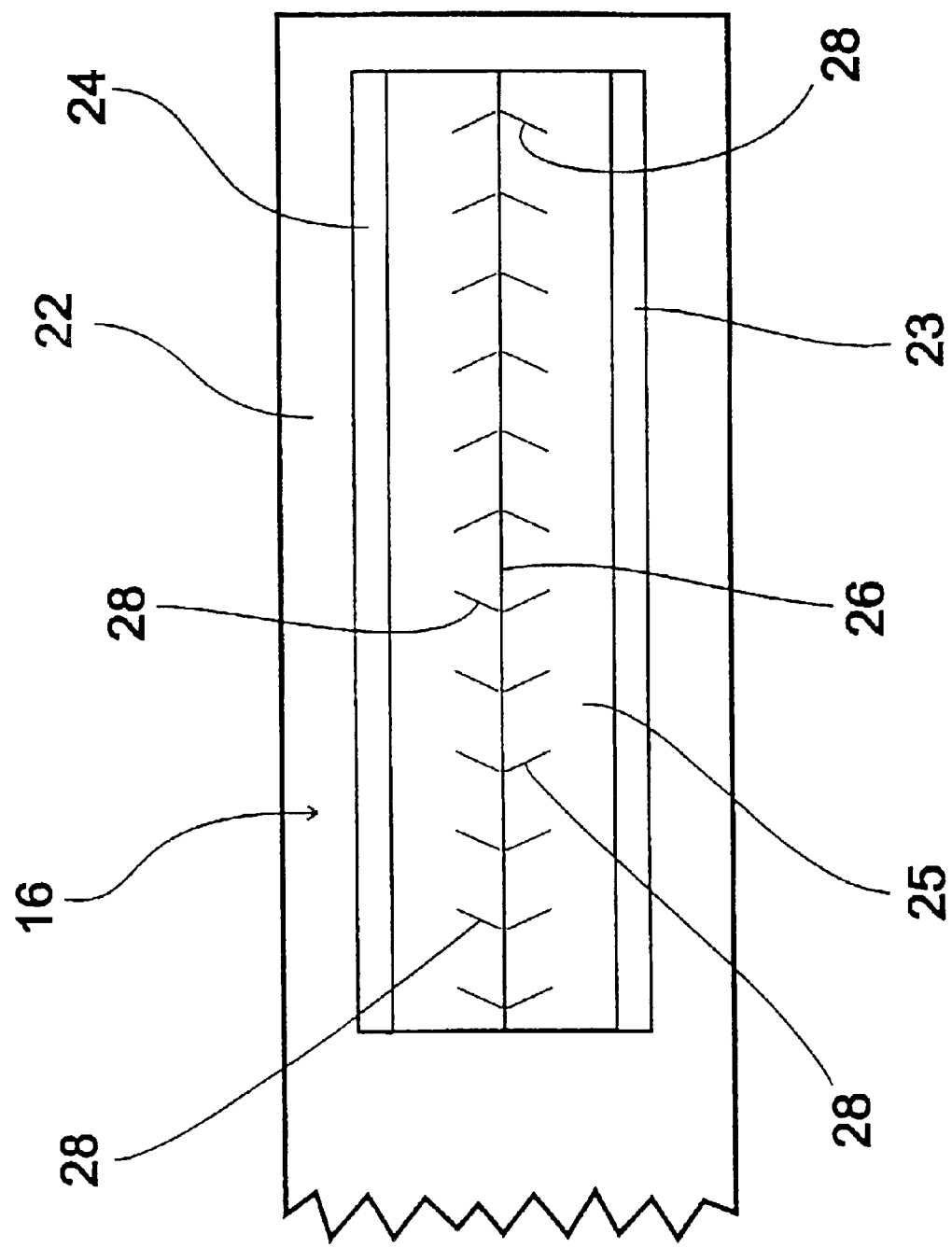

FIG. 7 and FIG. 8 show, in plan view, further configurations of clamping bodies 25 for clamping rails 16 according to FIG. 1 and FIG. 2. In the configuration according to FIG. 7, the clamping slit 26 is rectilinear in the longitudinal direction of the clamping rail 16. To increase the frictional forces, a number of transverse slits 27 are incorporated in the clamping body 25 which are at right angles to the clamping slit 26 and which wedge fast when a tensile force is exerted on an inserted guide wire or catheter shaft. In the configuration according to FIG. 8, the clamping slit 26 is likewise rectilinear in the longitudinal direction of the clamping rail 16, but, in contrast to the configuration according to FIG. 7, a number of oblique slits 28 are incorporated in the clamping body 25 and oriented obliquely with respect to the clamping slit 26. The oblique slits 28 are arranged in two groups facing in mutually opposite directions in order to increase the frictional forces in both directions by wedging when tensile forces are exerted.

Figure 9:
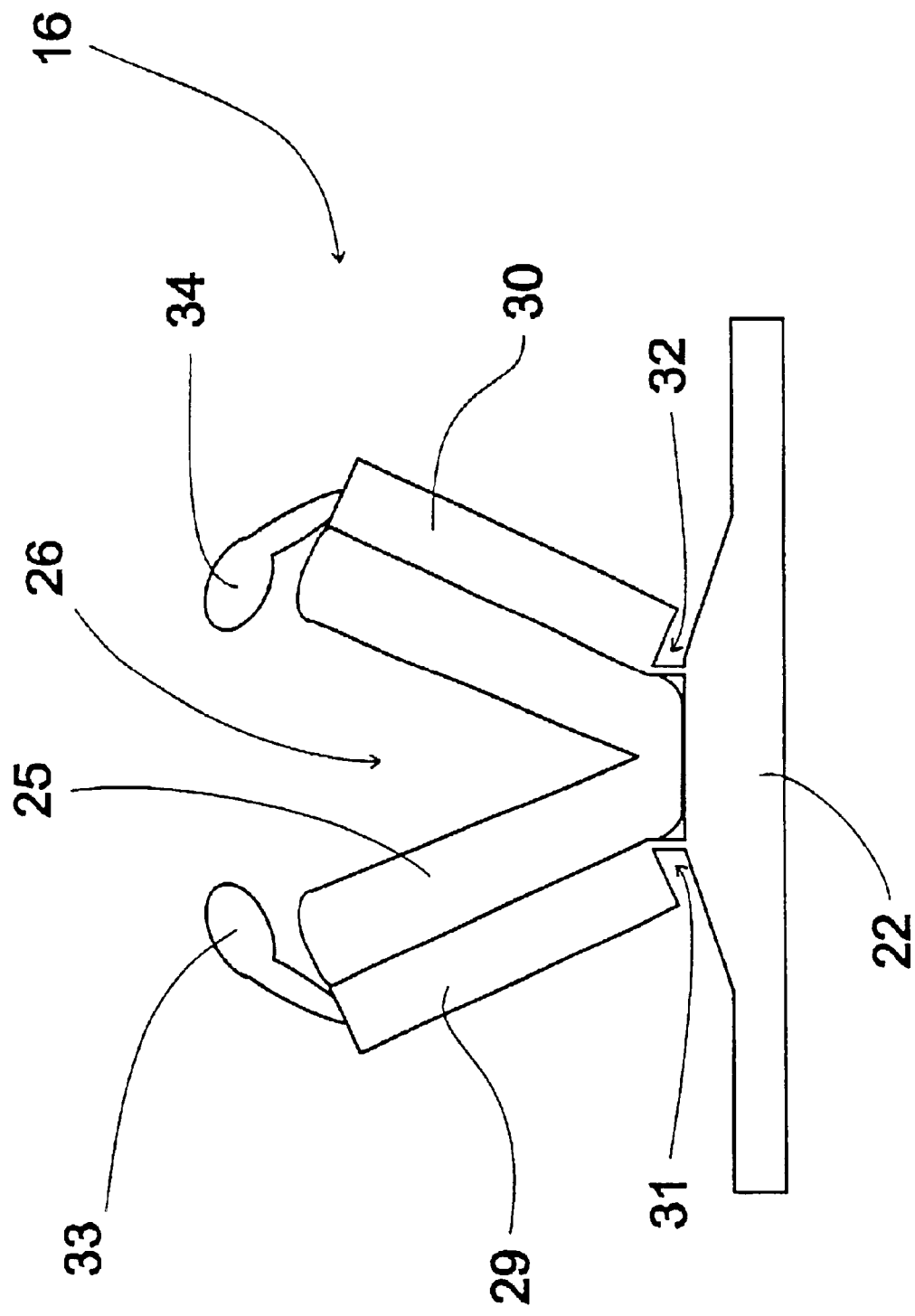
FIG. 9 shows, in cross section, a configuration of a clamping rail with tiltable side cheeks.

FIG. 9 shows, in cross section, a configuration of a clamping rail 16 which, like the clamping rails 16 shown in FIG. 1 to FIG. 3 and FIG. 5 to FIG. 8, has a base plate 22 and a clamping body 25 in which a clamping slit 26 is formed. The clamping rail 16 according to FIG. 9 is designed with a tiltable first side cheek 29 and with a tiltable second side cheek 30 which are connected to the base plate 22 via a first hinge 31 and a second hinge 32, respectively. In the configuration according to FIG. 9, the hinges 31, 32 are designed as webs which are relatively thin compared to the thickness of the tiltable side cheeks 29, 30 and which have sufficient elasticity for tilting of the side cheeks 29, 30 and a degree of safety against breaking which is sufficient for at least several dozen tilting maneuvers.

Arranged at the ends of the tiltable side cheeks 29, 30 directed away from the hinges 31, 32, there is a locking device in the form of a snap-fit closure which is made up of a first snap-fit lug 33 and a second snap-fit lug 34 and in which, in the closed position, the snap-fit lugs 33, 34 engage one behind the other with substantially parallel alignment of the tiltable side cheeks 29, 30. To open the tiltable side cheeks 29, 30, the snap-fit closure can be opened by means of the snap-fit lugs 33, 34, which each have a rounded thickened part at the end, being prized apart from one another by hand.

Figure 10:
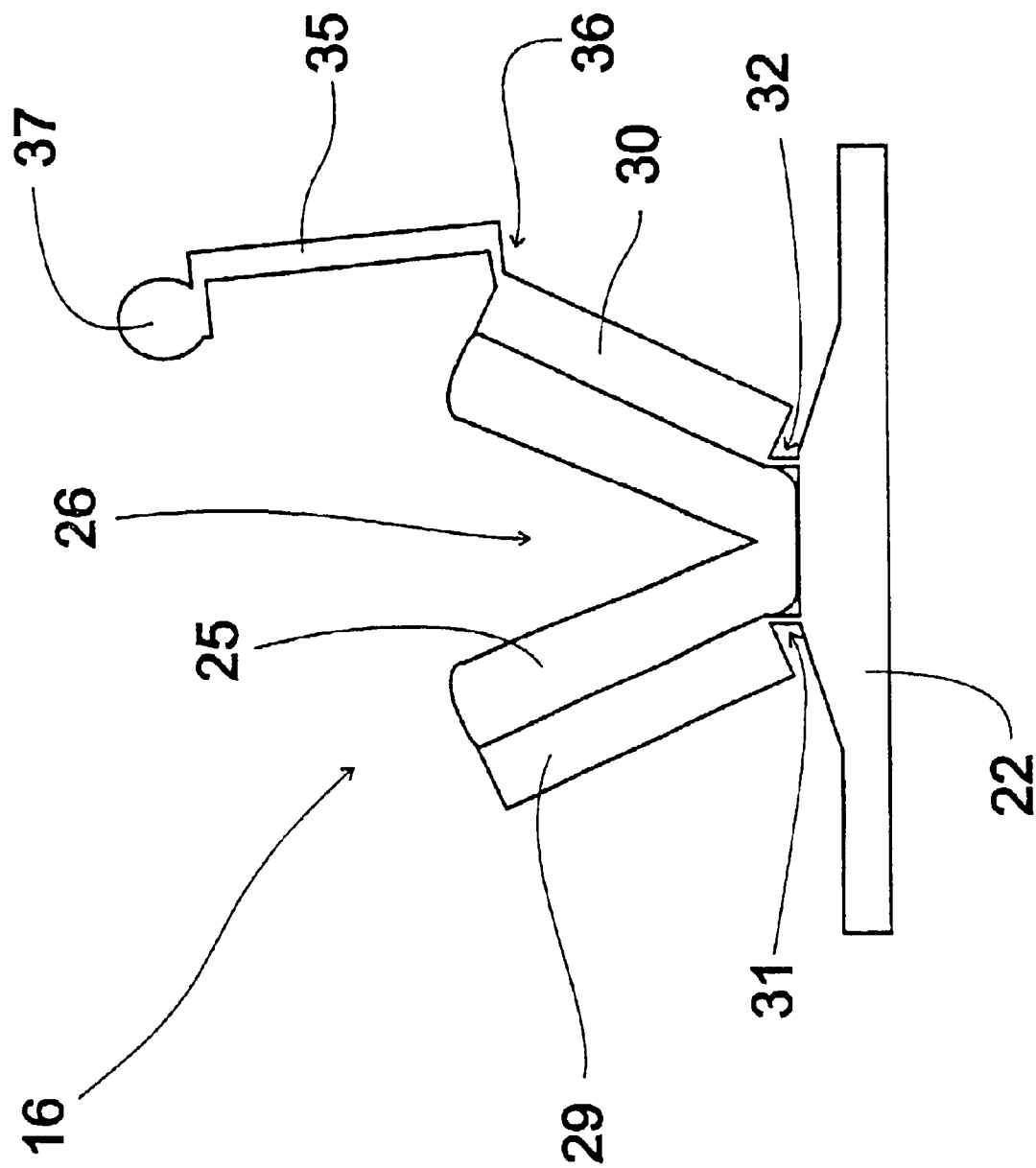
FIG. 10 shows, in cross section, a further configuration of a clamping rail with tiltable side cheeks.

FIG. 10 shows, in cross section, a further configuration of a clamping rail 16 with tiltable side cheeks 29, 30 in accordance with the configuration according to FIG. 9, but with the locking device, in contrast to the configuration according to FIG. 9, being formed by a tilting bracket 35. The tilting bracket 35 is connected via a bracket hinge 36, designed as a web in the configuration according to FIG. 10, to that end of a tiltable side cheek 29, 30 which is directed away from the particular hinge 31, 32 and, at the end which is remote from the bracket hinge 36 it is angled off at a right angle and, to facilitate handling, is provided with an actuating button 37 in the area of the angled-off portion. To close the clamping slit 26, the tiltable side cheeks 29, 30 are moved toward one another and, when they are in substantially parallel orientation to one another, the tilting bracket 35 is maneuvered so that the angled portion engages behind the side cheek 29, 30 lying opposite the bracket hinge 36.

Figure 11:
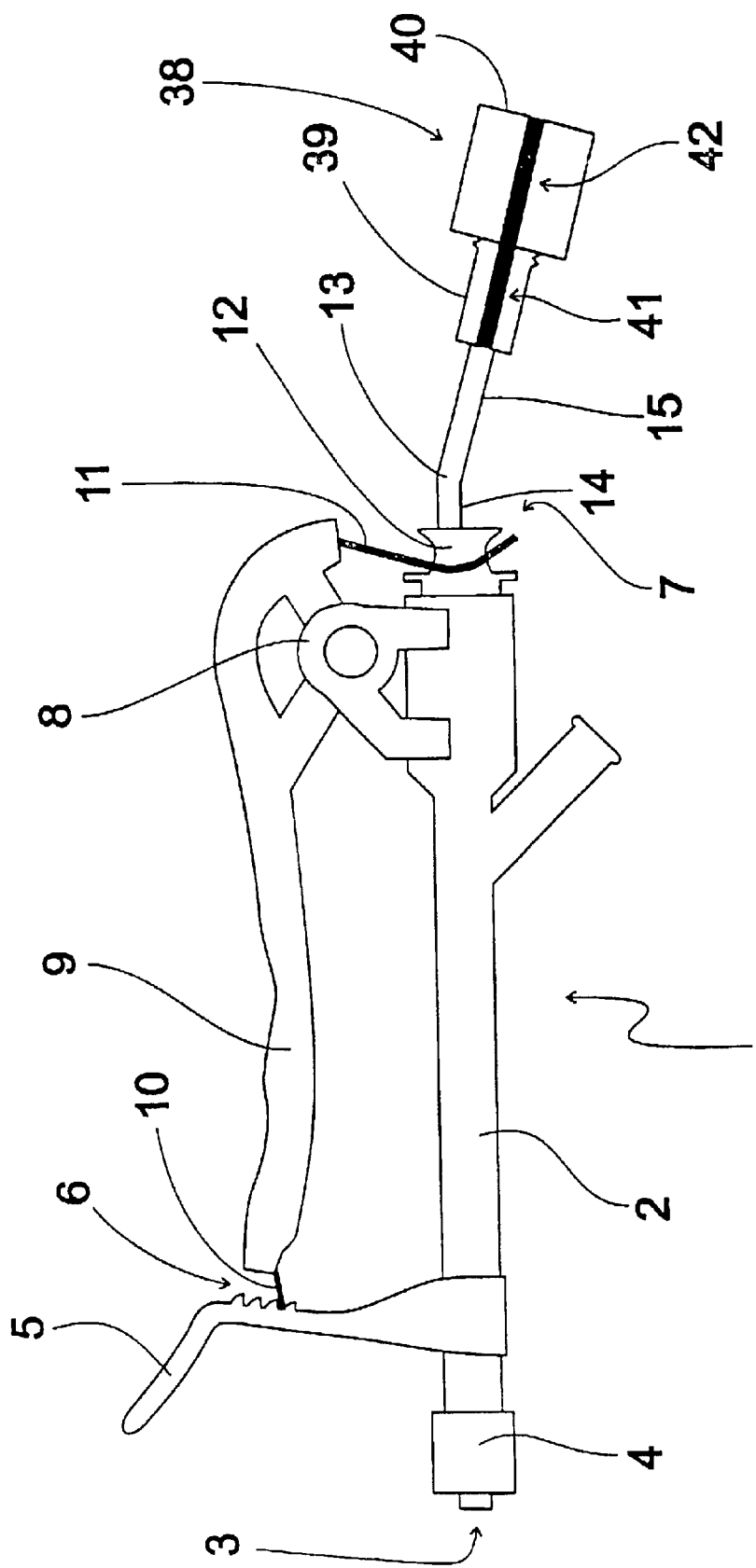
FIG. 11 shows a side view of an introduction valve with a fixing arm on which a clamping sleeve arrangement is fitted.

FIG. 11 shows, in a side view, an introduction valve 1 which is designed in accordance with the illustrative embodiments shown in FIG. 1 to FIG. 4 and which has a fixing arm 13 on which a clamping sleeve arrangement 38 is arranged as the clamping unit of a clamping device. The clamping sleeve arrangement 38 has a clamping sleeve 39 which is connected in a rotationally fixed manner to the holding portion 15 of the fixing arm 13, and a screw sleeve 40 which can be turned in relation to the clamp sleeve 39. The clamping sleeve 39 has a clamping sleeve groove 41 which, in the insertion position shown in FIG. 11, is aligned with a screw sleeve groove 42 formed in the screw sleeve 40 so that for example a guide wire can be introduced into the clamping sleeve arrangement 38.

Figure 12:
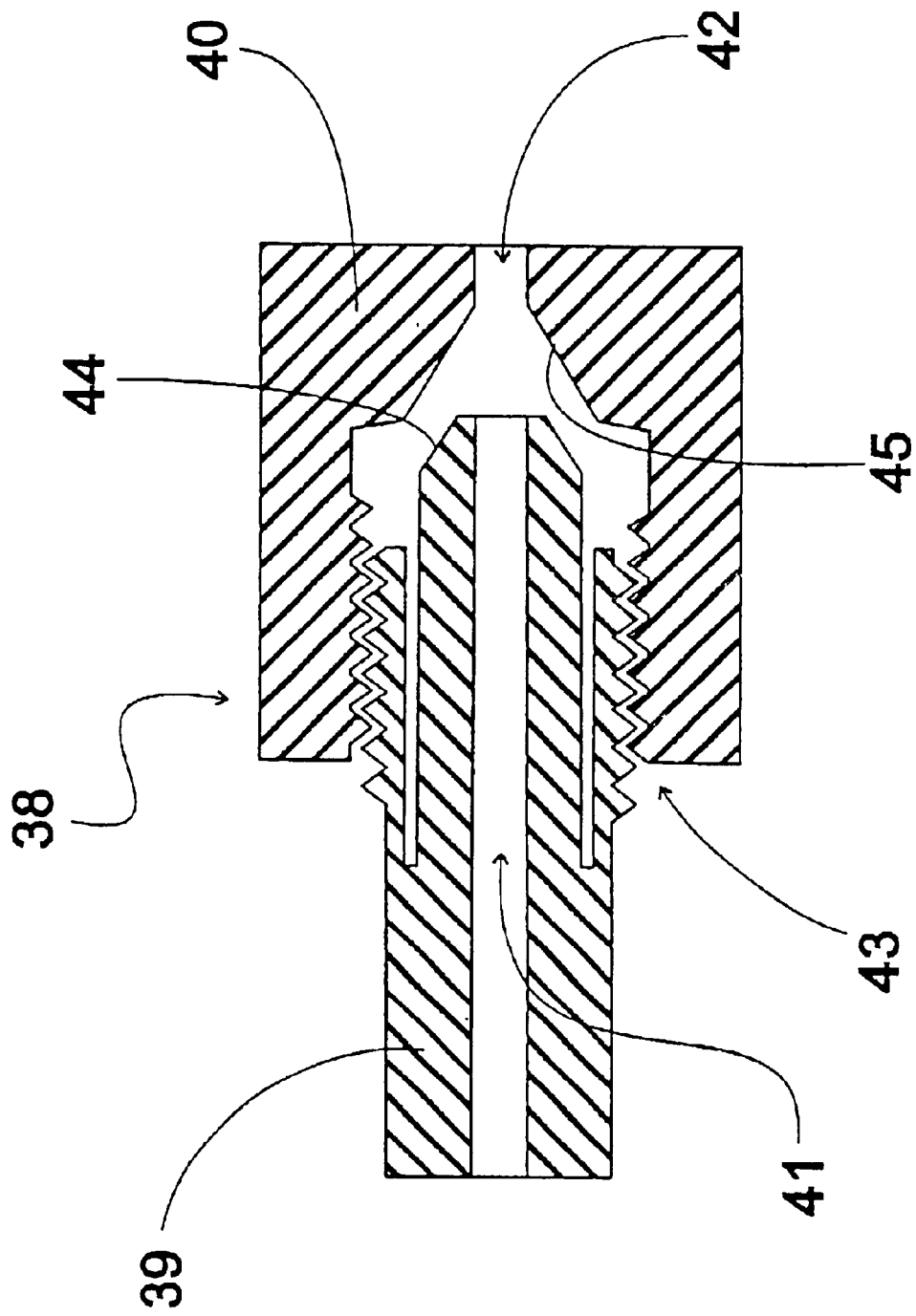
FIG. 12 shows, in cross section, the clamping sleeve arrangement according to FIG. 11 in an insertion position.

FIG. 12 shows, in cross section, the clamping sleeve arrangement 38 according to FIG. 11 in the insertion position. It will be seen from FIG. 12 that the clamping sleeve 39 and the screw sleeve 40 are connected to one another in a rotatable manner via a thread 43, the clamping sleeve 39 engaging partially in the screw sleeve 40. At their ends pointing toward each other, the clamping sleeve 39 and the screw sleeve 40 are designed with mutually complementary bevels 44, 45 which, in the insertion position, are spaced apart from one another or lie against one another without any substantial deformation of the end of the clamping sleeve 39 engaging in the clamping screw 40.

Figure 13:
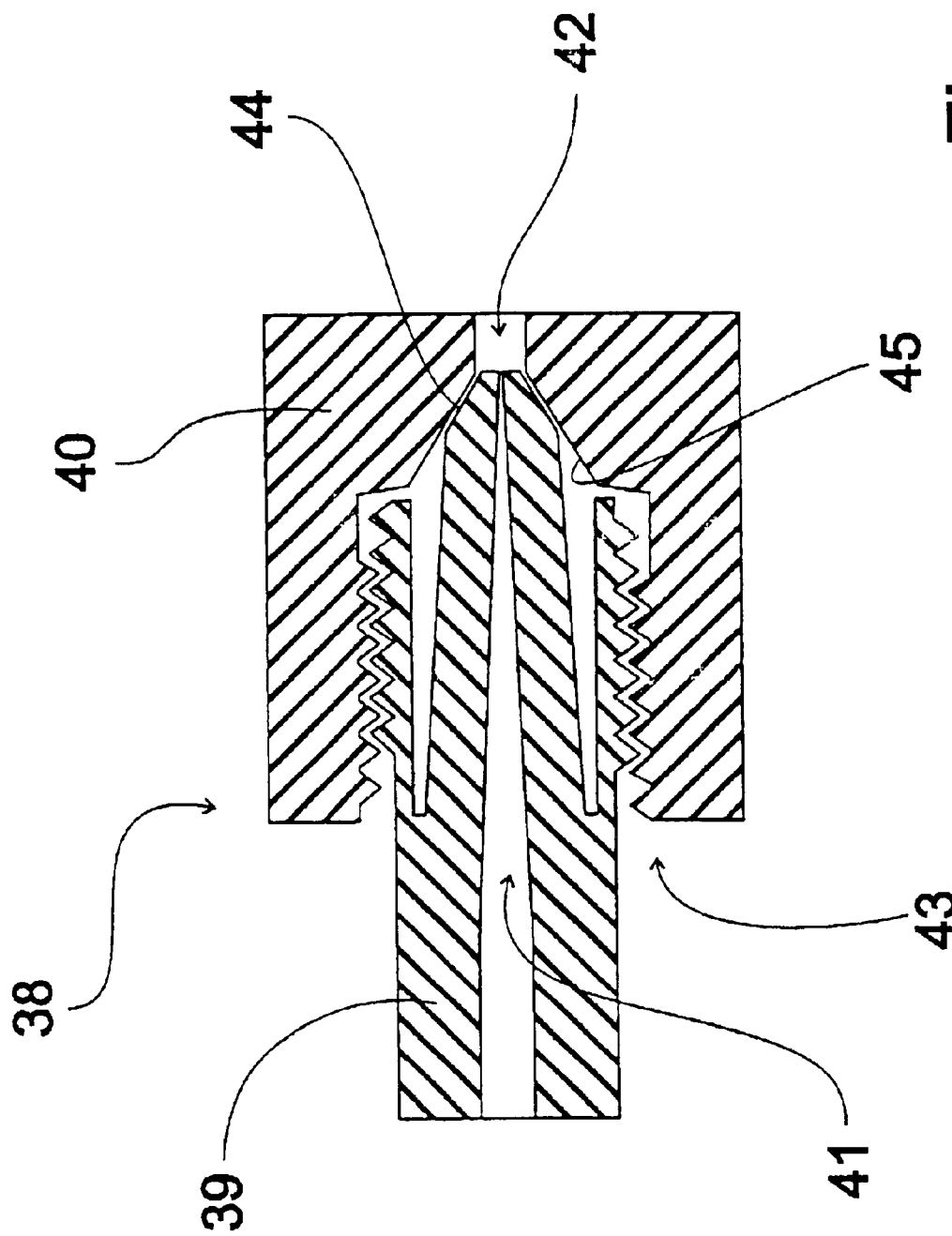
FIGS. 13 and 14 show a cross section and a side view, respectively, of the clamping sleeve arrangement according to FIG. 11, in a fixing position.
Figure 14:
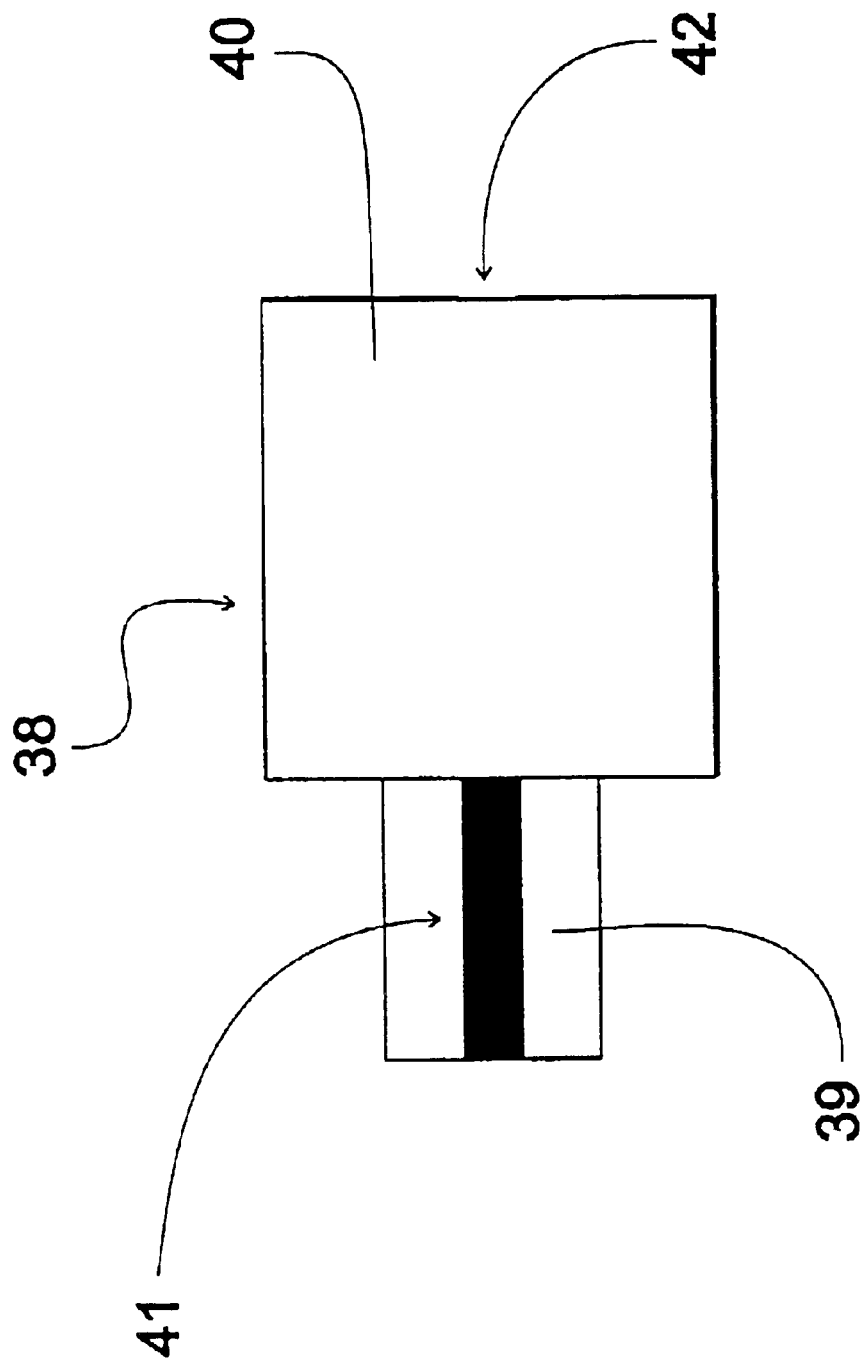

FIG. 13 and FIG. 14 show, in cross section and side view, respectively, the clamping sleeve arrangement 38 according to FIG. 11 in a fixing position in which the screw sleeve 40 is screwed onto the clamping sleeve 39 to such an extent that the bevels 44, 45 of the clamping sleeve 39 and of the screw sleeve 40, respectively, come into engagement with one another and slide against one another, narrowing the clamping sleeve groove 41 in the end area.

It can be seen from FIG. 14 that, in the fixing position, the clamping sleeve groove 41 and the screw sleeve groove 42, not visible in the illustration according to FIG. 14, are twisted in relation to one another.

Figure 15:
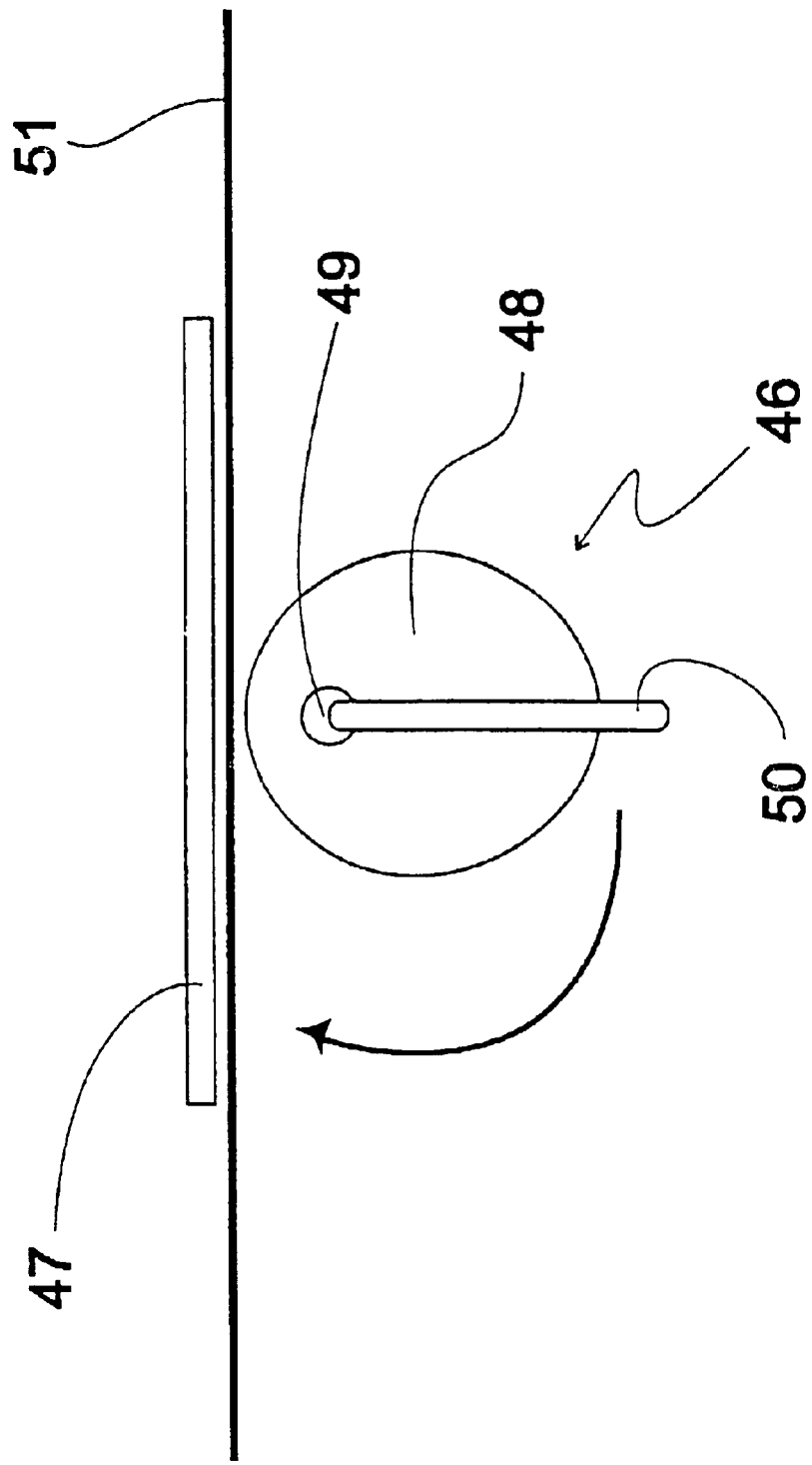
FIGS. 15 and 16 show, in plan view, a pivot body arrangement in an insertion position and in a fixing position, respectively.

Thus, in the fixing position of the clamping sleeve arrangement 38, a guide wire or catheter shaft which has been inserted into the clamping sleeve groove 41 and the screw sleeve groove 42 is secured against longitudinal displacement. To remove the guide wire or catheter shaft, the screw sleeve 40 must be turned relative to the clamping sleeve 39 until the clamping sleeve groove 41 is once again sufficiently opened and aligned with the screw sleeve groove 42. FIG. 15 shows, in a plan view, a pivot body arrangement 46 which can be connected to an introduction valve 1, for example according to FIG. 1 to FIG. 4 (not shown in FIG. 15), in an insertion position. The pivot body arrangement 46 has a counterplate 47 which is connected to a fixing arm 13 (not shown in FIG. 15) for securing on an introduction valve 1 or is made integral thereto. The pivot body arrangement 46 is also equipped with a compressible pivot body 48 which can pivot about an axis 49. The axis 49 is arranged at a distance from the counterplate 47 greater than the smallest material thickness between the axis 49 and the outside of the pivot body 48. To actuate the pivot body 48, a lever 50 is provided which is connected to the pivot body 48.

In the illustrative embodiment show in FIG. 15, the pivot body 48 is of elliptical design and the axis 49 is arranged eccentrically, for example in the area of a focal point. In the insertion position shown in FIG. 15, with appropriate alignment of the lever 50, an interspace is present between the counterplate 47 and that side of the pivot body 48 facing toward the counterplate 47, into which interspace a guide wire 51, for example, can be inserted.

Figure 16:
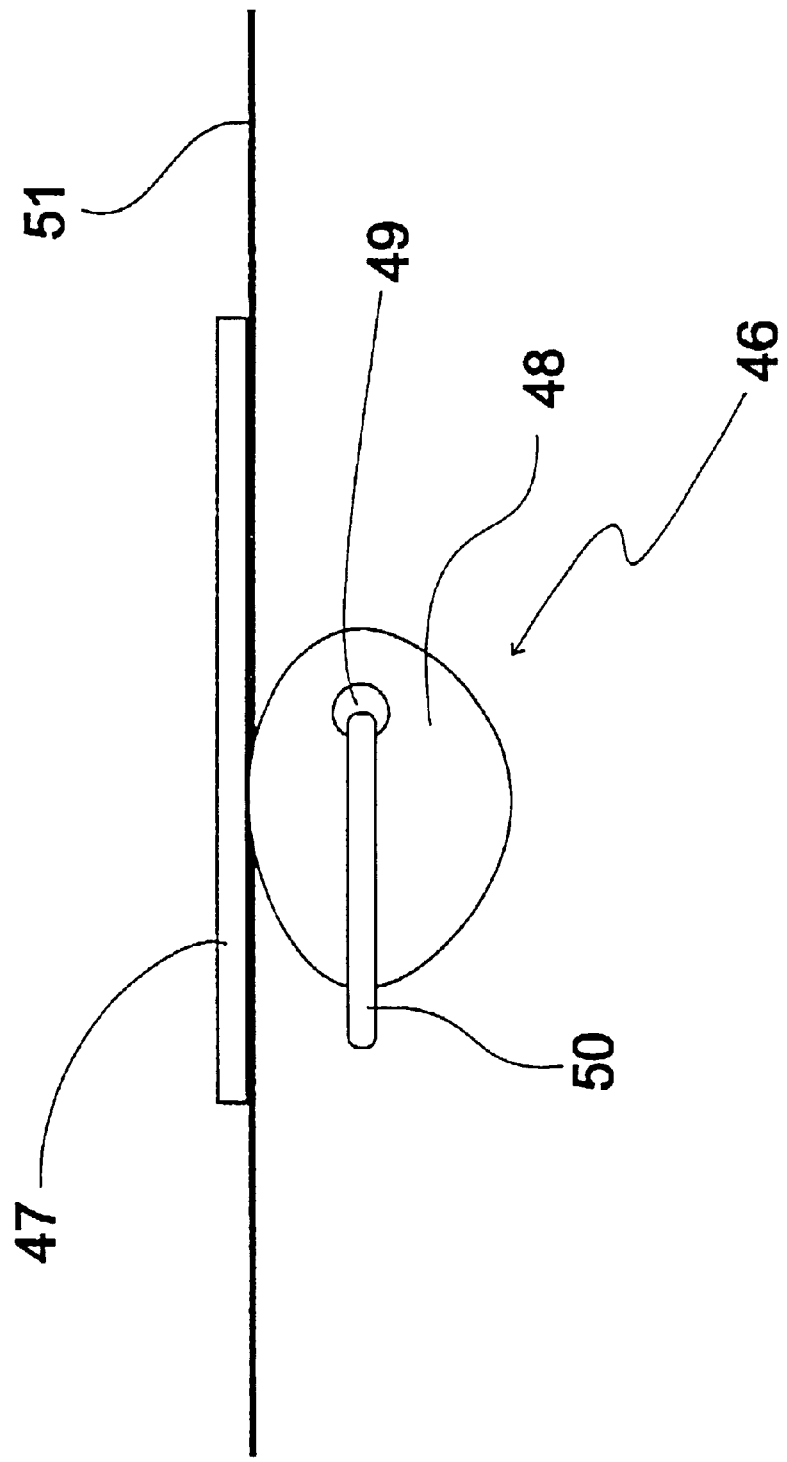

FIG. 16 shows the pivot body arrangement 46 according to FIG. 15 in a fixing position in which the lever 50 has been moved and the pivot body 48 is pressed onto the counterplate 47 in order to secure the guide wire 51 against longitudinal displacement. In the fixing position shown in FIG. 16, the lever 50 can be fixed with locking means not shown in FIG. 16.

What is claimed is:

1. A device for handling at least one guide wire in order to guide an invasive medical instrument or for handling a catheter shaft in invasive medical techniques, with a fixing arm which can be secured on an introduction valve, and with a clamping device which is arranged on the fixing arm and with which the particular guide wire or catheter shaft can be secured against longitudinal displacement, wherein the fixing arm protrudes beyond an introduction end of the introduction valve.

2. A device according to claim 1, characterized in that the fixing arm can be secured on the introduction valve in a releasable manner via a groove-and-tongue connection.

3. A device according to claim 1, characterized in that the fixing arm can be secured on the introduction valve in a releasable manner via a plug connection.

4. A device according to claim 2, characterized in that an adapter piece is provided with which the fixing arm can be secured in a releasable manner on the introduction valve.

5. A device according to claim 1, characterized in that the fixing arm is connected rigidly to the introduction valve.

6. A device according to claim 1, characterized in that the fixing arm has a securing portion and a holding portion which is angled off in relation to the securing portion.

7. A device according to claim 1, characterized in that the fixing arm has a securing portion and a holding portion designed as a holding plate.

8. A device according to claim 1, characterized in that the clamping device has a clamping unit for fixing a guide wire.

9. A device according to claim 1, characterized in that the clamping device has at least two clamping units which are arranged laterally spaced apart from one another and are used for fixing two guide wires or one guide wire and a catheter shaft.

10. A device according to claim 1, characterized in that the clamping device has three or four clamping units which are arranged laterally spaced apart from one another and are used for fixing guide wires and/or catheter shafts.

11. A device for handling at least one guide wire in order to guide an invasive medical instrument or for handling a catheter shaft in invasive medical techniques, with a fixing arm which can be secured on an introduction valve, and with a clamping device which is arranged on the fixing arm and with which the particular guide wire or catheter shaft can be secured against longitudinal displacement, wherein the clamping device has, as clamping unit, at least one elongated clamping rail which has a holder part with a base plate and two side cheeks and has a clamping body inserted into the holder part and designed with a longitudinally extending clamping slit.

12. A device according to claim 11, characterized in that the base plate and the side cheeks are connected rigidly to one another and at right angles to one another.

13. A device according to claim 11, characterized in that the side cheeks are each arranged pivotably on the base plate via a respective hinge, and in that a locking device is provided for fixing the side cheeks with the clamping slit closed.

14. A device according to claim 13, characterized in that the locking device has two snap-fit lugs which engage one behind the other in the closed position of the side cheeks.

15. A device according to claim 13, characterized in that the locking device has a tilting bracket which at one end is articulated on one side cheek and, in the closed position, engages over the other side cheek.

16. A device according to claim 11, characterized in that the clamping slit is undulating.

17. A device according to claim 11, characterized in that the clamping body has slits which are oriented transversely or obliquely with respect to the clamping slit.

18. A device for handling at least one guide wire in order to guide an invasive medical instrument or for handling a catheter shaft in invasive medical techniques, with a fixing arm which can be secured on an introduction valve, and with a clamping device which is arranged on the fixing arm and with which the particular guide wire or catheter shaft can be secured against longitudinal displacement, wherein the clamping device has at least one clamping sleeve arrangement with a clamping sleeve and a screw sleeve which are designed with grooves that can be aligned relative to one another and are intended to receive a guide wire or a catheter shaft, the cross section of the clamping sleeve decreasing at least in stages in a direction of rotation.

19. A device for handling at least one guide wire in order to guide an invasive medical instrument or for handling a catheter shaft in invasive medical techniques, with a fixing arm which can be secured on an introduction valve, and with a clamping device which is arranged on the fixing arm and with which the particular guide wire or catheter shaft can be secured against longitudinal displacement, wherein the clamping device has a counterplate and a rotatably mounted pivot body which, in a first pivot position, is at a distance from the counterplate, and, in a second pivot position, bears in part on the counterplate.

20. A device according to claim 19, characterized in that the pivot body has a circular cross section and is mounted eccentrically.

21. A device according to claim 19, characterized in that the pivot body has an elliptical cross section.

22. A device according to claim 21, characterized in that the pivot body is mounted centrally.

23. A device according to claim 21, characterized in that the pivot body is mounted in the area of a focal point.

24. A device for handling at least one guide wire in order to guide an invasive medical instrument or for handling a catheter shaft in invasive medical techniques, with a fixing arm adapted to be releasably secured on an introduction valve, and with a clamping device which is arranged on the fixing arm and with which the particular guide wire or catheter shaft can be secured against longitudinal displacement.

* * * * *